US00PP24684P2

(12) United States Plant Patent
Willemsen

(10) Patent No.: US PP24,684 P2
(45) Date of Patent: Jul. 22, 2014

(54) ***BRUNNERA* PLANT NAMED 'SEA HEART'**

(50) Latin Name: *Brunnera macrophylla*
Varietal Denomination: Sea Heart

(71) Applicant: Peter Jan Willemsen, Veenendaal (NL)

(72) Inventor: Peter Jan Willemsen, Veenendaal (NL)

( * ) Notice: Subject to any disclaimer, the term of this patent is extended or adjusted under 35 U.S.C. 154(b) by 93 days.

(21) Appl. No.: 13/694,253

(22) Filed: Nov. 13, 2012

(51) Int. Cl.
*A01H 5/00* (2006.01)

(52) U.S. Cl.
USPC ..... Plt./412

(58) Field of Classification Search
USPC ..... Plt./412
See application file for complete search history.

*Primary Examiner* — Annette Para
(74) *Attorney, Agent, or Firm* — Penny J. Aguirre

(57) ABSTRACT

A new cultivar of *Brunnera macrophylla*, 'Sea Heart', characterized by its leaves that are large, strong, round-cordate in shape, conspicuously mottled with silver between green veins, its resistance to sun scorch, and its vigorous growth habit.

2 Drawing Sheets

Botanical classification: *Brunnera macrophylla.*
Cultivar designation: 'Sea Heart'.

CROSS REFERENCE TO A RELATED APPLICATION

This application is co-pending with a U.S. Plant Patent Application filed for a plant derived from the same parentage that is entitled *Brunnera* Plant Named 'Silver Heart' (U.S. Plant patent application Ser. No. 13/694,529).

BACKGROUND OF THE INVENTION

The present invention relates to a new and distinct cultivar of *Brunnera macrophylla*, and is hereinafter referred to by the cultivar name 'Sea Heart'. 'Sea Heart' represents a new herbaceous perennial grown for use as a landscape plant.

The inventor discovered the new cultivar, 'Sea Heart', in August of 2010 as a naturally occurring chimeral mutation of *Brunnera macrophylla* 'Silver Lace' (not patented) that was spontaneously growing in a container in a production block of 'Silver Lace' in Veenendaal, The Netherlands.

Asexual propagation of the new cultivar was first accomplished under the direction of the Inventor by tissue culture in January of 2011 in Heerhugowaard, The Netherlands. Propagation by tissue culture has determined the characteristics to be stable and reproduced true to type in successive generations.

SUMMARY OF THE INVENTION

The following traits have been repeatedly observed and represent the characteristics of the new cultivar. These attributes in combination distinguish 'Sea Heart' as a new and unique cultivar of *Brunnera.*

1. 'Sea Heart' exhibits large and strong foliage.
2. 'Sea Heart' exhibits mature leaves that are conspicuously mottled with silver between green veins.
3. 'Sea Heart' exhibits mature leaves that are round-cordate in shape.
4. 'Sea Heart' exhibits resistance to sun scorch.
5. 'Sea Heart' exhibits a vigorous growth habit.

'Silver Lace', the parent plant of 'Sea Heart', differs from 'Sea Heart' in having leaves that are thinner, weaker, prone to sun scorch, and exhibit less conspicuous coloration. 'Sea Heart' can be most closely compared to the cultivars 'Jack Frost' (U.S. Plant Pat. No. 13,859), 'Silver Wings' (U.S. Plant Pat. No. 13,706), 'Emerald Mist' (U.S. Plant Pat. No. 20,460) and Mr. Morse (U.S. Plant Pat. No. 19,947), and 'Silver Heart'. 'Jack Frost' differs from 'Sea Heart' in having leaves that are thinner, weaker, less rounded in shape, and prone to sun scorch. 'Silver Wings' differ from 'Sea Heart' in leaves that are less rounded with less distinct silver mottling with a thin white margin. 'Emerald Mist' differs from 'Sea Heart' in having leaves with silver mottling on the outer portion of the leaf blade with leaf centers green in color. 'Mr. Morse' differs from 'Sea Heart' in having leaves that are less rounded with slightly less silver mottling and in having white flowers. 'Silver Heart' is similar to 'Sea Heart' in having round-cordate strong leaves that are sun tolerant, however 'Silver Heart' differs in having leaves with much more silver mottling.

BRIEF DESCRIPTION OF THE DRAWING

The accompanying colored photographs illustrate the overall appearance and distinct characteristics of the new *Brunnera*. The photographs were taken of a plant about one year in age as field grown outdoors and placed in a two-gallon container for the photographs.

The photograph in FIG. 1 provides a side view of 'Sea Heart' in bloom.

Figure 1:
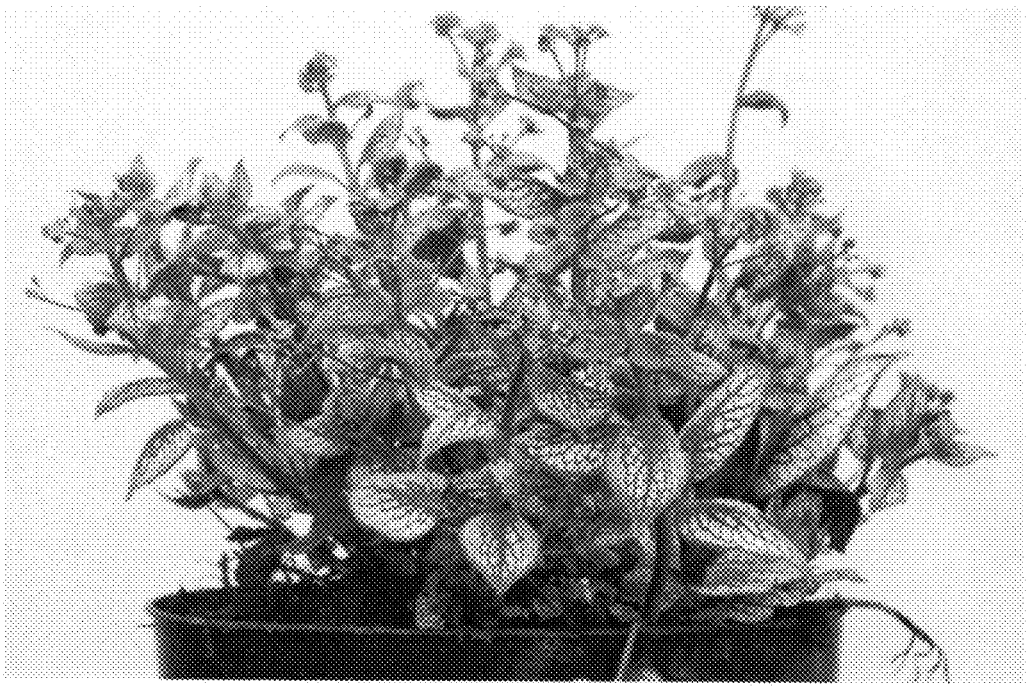
Figure 2:
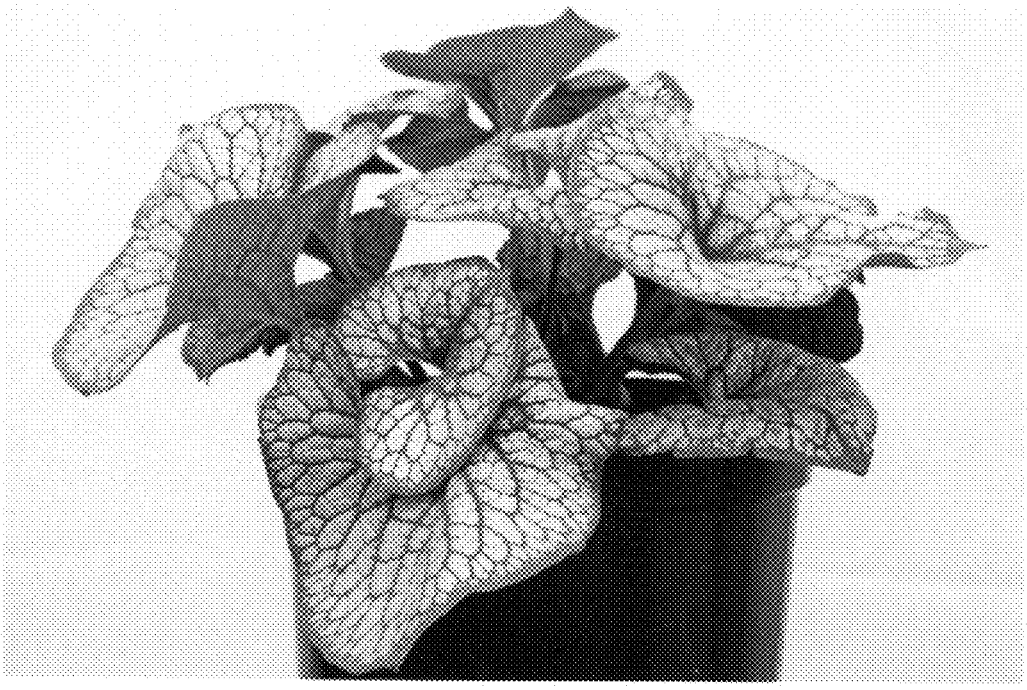

The photograph in FIG. 2 provides a side view of 'Sea Heart' in late summer.

Figure 3:
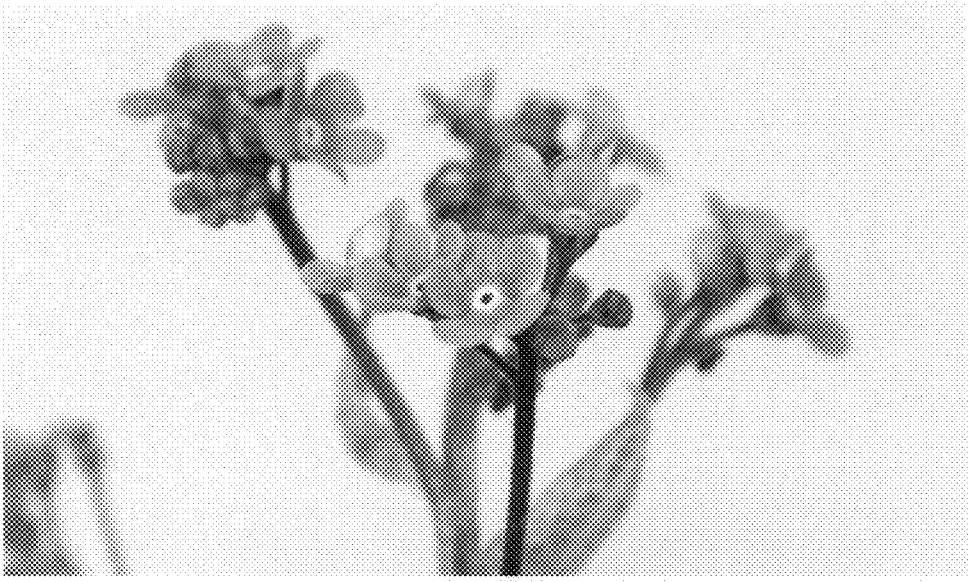

The photograph in FIG. 3 provides a close-up view of the flowers of 'Sea Heart'.

Figure 4:
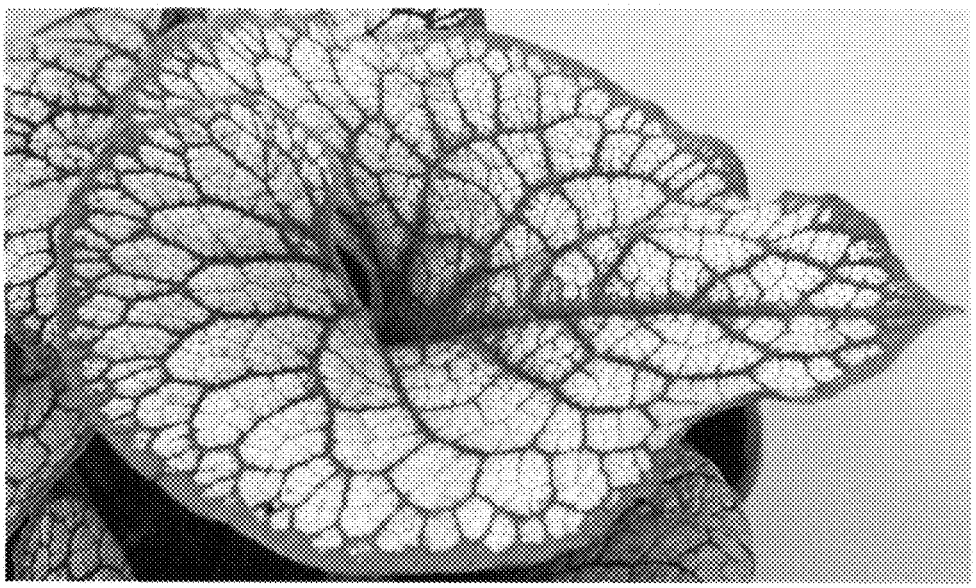

The photograph in FIG. 4 provides a close-up view of a mature leaf of 'Sea Heart'.

The colors in the photographs may differ slightly from the color values cited in the detailed botanical description, which accurately describe the colors of the new *Brunnera.*

DETAILED BOTANICAL DESCRIPTION OF THE PLANT

The following is a detailed description of one year-old plants of the new cultivar as field grown in Zuidwolde, The Netherlands. Plants were grown under average day temperatures ranging from 14° to 28° C. (August) to 8° to 16° C. (April) and average night temperatures of 6° to 16° C. (August) to 3° to 10° C. (April). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—April in The Netherlands.

*Plant type*.—Herbaceous perennial.

*Plant habit*.—Clump-forming, open mound with flowering stems emerging from basal rosette of foliage.

*Height and spread*.—Average of 27.4 cm in height, average of 40 cm in spread.

*Hardiness*.—At least hardy in U.S.D.A. Zones 3 to 9.

*Diseases and pests*.—No more susceptible or resistant to pests and diseases than other *Brunnera* varieties.

*Root description*.—Fibrous, medium in thickness and sparse in density.

*Branching habit*.—No lateral branches, leaves grow in basal rosettes, flowering stems arise from the centers of the rosettes before the mature leaves are formed.

*Propagation*.—Tissue culture.

*Growth rate*.—Vigorous.

Stem description (flowering stem):

*Shape*.—Round.

*Stem color*.—146B, tinged with N199A.

*Stem size*.—An average of 21.9 cm in length and 0.5 mm in diameter.

*Stem surface*.—Moderately glossy, angulate.

*Stem aspect*.—Average angle of 60° to soil.

*Stem strength*.—Strong.

*Stem number*.—An average of 32 main flowering stems.

*Internode*.—Average length is 1.8 cm (cauline leaves).

Foliage description:

*Leaf shape*.—Round-cordate.

*Leaf division*.—Single.

*Leaf base*.—Oblique, lobes at the base moderately overlapping.

*Leaf apex*.—Broad acute.

*Leaf venation*.—Pinnate-laciniate, color: upper surface; 137C, lower surface; 148A to 148B.

*Leaf margins*.—Entire.

*Leaf attachment*.—Petiolate.

*Leaf arrangement*.—Alternate on cauline leaves and basal leaves are in rosettes.

*Leaf surface*.—Upper surface is slightly glossy and rugose, lower surface is dull and rugose, both surfaces are rough to the touch due to being heavily pubescent; short scabrous hairs are an average of 0.7 mm in length and a color between 155A and 156D.

*Leaf substance*.—Strong.

*Leaf variegation pattern*.—Silver mottled between green veins, green margins.

*Leaf color*.—Young upper surface; 191B veined 141B, young lower surface; 138A, mature upper surface; 192B with a silvery shine, margins, veins and tissue surrounding veins 137B, mature lower surface; 137C.

*Leaf size*.—Mature leaves, an average of 17.3 cm in length and 14.3 cm in width.

*Leaf quantity*.—Average of 5 per rosette.

*Cauline leaves*.—Average of 5, ovate in shape, sessile, average of 8 cm in length and 7 cm in width, acute apex, cuneate base, color, venation and surface match basal leaves (with slightly less mottling).

*Petioles*.—Average of 12.5 cm in length and 5 mm in width, 144A in color and strongly tinged with 200A.

Flower description:

*Inflorescence type*.—Terminal paniculate cymes of rotate flowers on leafy flowering stems that arise from base with smaller panicles on upper nodes.

*Inflorescence size*.—Average of 4.6 cm in height and about 1.7 cm in width.

*Flower fragrance*.—Faint, sweet and somewhat unpleasant.

*Flower quantity*.—Average of 15 per inflorescence, 150 per flowering stem.

*Flower lastingness*.—Average of one week, self-cleaning.

*Flower buds*.—Broadly obovate in shape with top flattened, average of 2.5 mm in diameter and 2 mm in depth, approximately 30% of the flower buds open at one stage, 90B with green base 143C in color.

*Flower aspect*.—Held upright to slightly outward.

*Flower size*.—Average of 9 mm in diameter and 4 mm in depth.

*Petals*.—Rotate, average of 5, broadly obovate in shape, lower 20% fused at base, margin is entire, apex is rounded, upper and lower surfaces are dull and moderately velvety, about 4.5 mm in length and 3 mm in width, color: when opening upper side; 95C, base 85A turning to N155A, when opening lower side; 91A, when fully opened upper side; a color between 99D and 100A, base N155A, when fully opened lower side; 97A, petal color fading to 101B.

*Calyx*.—Campanulate, about 1.5 mm in width and 2 mm in length.

*Sepals*.—5, Rotate and campanulate, ovate in shape, about 2 mm in length and 0.75 mm in width, margin is entire, apex is acute, cuneate base lower 25% fused, upper surface smooth and slightly glossy, lower side dull and moderately pubescent and covered with small pubescent hairs 0.2 mm in length and 157D in color, color: immature upper surface; 143A to 143B, immature lower surface; 143B to 143C, mature upper surface; 143A, mature lower surface; 143B.

*Peduncles*.—Average of 4 cm in length and 1 mm in diameter, an average angle of 50° to main stem, moderately strong, and 147A in color.

*Pedicels*.—Average of 5 mm in length and about 0.5 mm in diameter, an average angle of 40° to main stem, moderately strong, and 147A in color.

Reproductive organs:

*Gynoecium*.—1 Pistil, about 1 mm in length, stigma is club-shaped and 145C in color, ovary is 0.8 mm in length and 145C in color, ovary is 144A to 144B in color.

*Androcoecium*.—5 stamens, anther is dorsifixed, kidney-shaped, about 0.5 mm in length and 203A in color, filament 0.5 mm in length and NN155D in color, pollen is low in quantity and 155D in color.

*Seed*.—No fruits or seed observed.

It is claimed:

1. A new and distinct cultivar of *Brunnera* plant named 'Sea Heart' as herein illustrated and described.

* * * * *